US009745262B2

(12) United States Patent
Barth et al.

(10) Patent No.: US 9,745,262 B2
(45) Date of Patent: Aug. 29, 2017

(54) PROCESS FOR CONTINUOUSLY PREPARING METHYL MERCAPTAN FROM CARBON COMPOUNDS, SULFUR AND HYDROGEN

(75) Inventors: Jan-Olaf Barth, Franfurt (DE); Christoph Weckbecker, Gruendau-Lieblos (DE); Hubert Redlingshoefer, Muenchsteinach (DE); Johannes A. Lercher, Ottobrunn (DE); Christoph Kaufmann, Haag (DE)

(73) Assignee: EVONIK DEGUSSA GMBH, Essen (DE)

( * ) Notice: Subject to any disclaimer, the term of this patent is extended or adjusted under 35 U.S.C. 154(b) by 698 days.

(21) Appl. No.: 12/837,017

(22) Filed: Jul. 15, 2010

(65) Prior Publication Data
US 2011/0015443 A1 Jan. 20, 2011

Related U.S. Application Data

(60) Provisional application No. 61/290,708, filed on Dec. 29, 2009.

(30) Foreign Application Priority Data

Jul. 20, 2009 (DE) .................. 10 2009 027 837

(51) Int. Cl.
| | |
|---|---|
| C07C 319/08 | (2006.01) |
| C07C 319/06 | (2006.01) |
| C07C 319/28 | (2006.01) |
| C07C 319/02 | (2006.01) |
| C01B 17/16 | (2006.01) |

(52) U.S. Cl.
CPC .......... C07C 319/02 (2013.01); C01B 17/161 (2013.01); C07C 319/08 (2013.01); *Y02P 20/127* (2015.11); *Y02P 20/582* (2015.11)

(58) Field of Classification Search
None
See application file for complete search history.

(56) References Cited

U.S. PATENT DOCUMENTS

| | | | |
|---|---|---|---|
| 2,565,195 | A | 8/1951 | Bell et al. |
| 4,057,613 | A | 11/1977 | Meadow et al. |
| 4,410,731 | A | 10/1983 | Buchholz |
| 4,665,242 | A | 5/1987 | Boulinguiez et al. |
| 4,822,938 | A | 4/1989 | Audeh et al. |
| 4,864,074 | A | 9/1989 | Han et al. |
| 5,852,219 | A | 12/1998 | Sauer et al. |
| 5,866,721 | A | 2/1999 | Hofen et al. |
| 7,569,731 | B2 | 8/2009 | Yang et al. |
| 7,592,288 | B2 | 9/2009 | Redlingshöfer et al. |
| 7,691,776 | B2 | 4/2010 | Redlingshöfer et al. |
| 2006/0135816 | A1 | 6/2006 | Redlingshöfer et al. |
| 2008/0033213 | A1 | 2/2008 | Redlingshöfer et al. |
| 2008/0293974 | A1 | 11/2008 | Barth et al. |
| 2010/0041548 | A1 | 2/2010 | Yang et al. |

FOREIGN PATENT DOCUMENTS

| | | |
|---|---|---|
| DE | 1 768 826 | 8/1971 |
| EP | 0 850 923 | 7/1998 |
| GB | 1 268 842 | 7/1968 |
| WO | 2005/021491 | 5/2005 |
| WO | 2005/040082 | 5/2005 |
| WO | 2006/015668 | 2/2006 |
| WO | 2006/063669 | 6/2006 |
| WO | 2009/083368 | 7/2009 |

OTHER PUBLICATIONS

Mashkina, et al., "Activity of Tungstate Catalysts in the Synthesis of Methyl-Mercaptane From Methanol and Hydrogen Sulfide", Reaction Kinetics and Catalysis Letters, vol. 36, No. 1, 159-164, 1988.
PCT International Search Report (Form PCT/ISA/210) for PCT/EP2010/060322 dated Oct. 7, 2010.
PCT Notification of Transmittal of the International Search Report and the Written Opinion of the International Searching Authority, or the Declaration (Form PCT/ISA/220) for PCT/EP2010/060322 dated Oct. 7, 2010.
PCT Written Opinion of the International Searching Authority (Form PCT/ISA/237) for PCT/EP2010/060322 dated Oct. 7, 2010.

*Primary Examiner* — Alicia Lotton
(74) *Attorney, Agent, or Firm* — Smith, Gambrell & Russell, LLP

(57) ABSTRACT

The invention relates to a process for continuously preparing methyl mercaptan by reacting a mixture comprising carbon compounds with sulfur and hydrogen, wherein the carbon disulfide and hydrogen sulfide compounds which form are subsequently converted to methyl mercaptan.

25 Claims, 3 Drawing Sheets

PROCESS FOR CONTINUOUSLY PREPARING METHYL MERCAPTAN FROM CARBON COMPOUNDS, SULFUR AND HYDROGEN

CROSS REFERENCE TO RELATED APPLICATION

The present application claims the benefit of U.S. Provisional Application No. 61/290,708 filed on Dec. 29, 2009.

The invention relates to a process for continuously preparing methyl mercaptan by reacting a mixture comprising carbon compounds with sulfur and hydrogen, wherein the carbon disulfide and hydrogen sulfide compounds which form are converted to methyl mercaptan.

Methyl mercaptan is an industrially important intermediate for the synthesis of methionine, and for the preparation of dimethyl sulfoxide and dimethyl sulfone. Methyl mercaptan is prepared predominantly from methanol and hydrogen sulfide by reaction over a catalyst consisting of an aluminum oxide support and transition metal oxides and basic promoters. The mercaptan is usually synthesized in the gas phase at temperatures between 300 and 500° C. and at pressures between 1 and 25 bar. The product gas mixture comprises, as well as the methyl mercaptan formed and water, the unconverted proportions of the methanol and hydrogen sulfide starting materials, and, as by-products, dimethyl sulfide and dimethyl ether, and also small amounts of polysulfides (dimethyl disulfide). Gases which are inert for the purposes of the reaction, for example carbon monoxide, carbon dioxide, nitrogen and hydrogen, are also present in the product gas.

The methyl mercaptan formed is removed from the product gas mixture, for example as explained in U.S. Pat. No. 5,866,721, in a plurality of distillation and scrubbing columns at temperatures between 10 and 140° C.

Methyl mercaptan can alternatively be prepared from carbon oxides, hydrogen, sulfur and/or hydrogen sulfide. According to U.S. Pat. No. 4,665,242, for example, methyl mercaptan is prepared using catalysts based on alkali metal tungstates. Compared to the methanol-based method, these processes have lower selectivities for methyl mercaptan and conversions of carbon oxides. U.S. Pat. No. 4,410,731 relates to a process and catalysts for the preparation of methyl mercaptan from carbon oxides, hydrogen and hydrogen sulfide or sulfur based on alkali metal molybdenum sulfides comprising transition metal oxides as promoters, and aluminum oxide as a support. WO2005/040082 claims a process and catalysts for the preparation of methyl mercaptan from carbon oxides, hydrogen and hydrogen sulfide or sulfur, based on alkali metal molybdates comprising transition metal oxides as promoters, in which silicon dioxide preferably serves as a support.

US 2008/0293974A1 claims a process and catalysts for the preparation of methyl mercaptan from carbon- and hydrogen-containing compounds, sulfur and/or oxygen based on alkali metal molybdates promoted with transition metal oxides.

The preparation of methyl mercaptan from carbon disulfide or carbonyl sulfide and hydrogen is a further alternative to the methanol-based method. However, the processes are characterized by comparatively low selectivities for methyl mercaptan, a multitude of by-products which are inconvenient and costly to remove, and the necessity of handling toxic carbon disulfide or carbonyl sulfide in large amounts.

U.S. Pat. No. 4,057,613 describes a catalyst-free process for preparing carbon disulfide from sulfur and hydrocarbons.

Bell et al. describe, in U.S. Pat. No. 2,565,195, a process for hydrogenating carbon disulfide to methyl mercaptan and dimethyl sulfide over Friedel-Crafts-type acidic catalysts ($AlCl_3$, $BF_3$). The by-products obtained include hydrogen sulfide, thioformaldehyde, trithiomethylene, methylenedithiol, methane and ethene.

Audeh et al. describe, in U.S. Pat. No. 4,822,938, the reaction of methane with sulfur to give carbon disulfide, methyl mercaptan and higher hydrocarbons. Catalysts based on Co—Ni systems and H-ZSM-5-zeolites are used. The aim of the reaction is the gradual formation of higher aliphatics and olefins based on methane in a Fischer-Tropsch-like reaction. Carbon disulfide and methyl mercaptan are considered here as intermediates. Disadvantages of the reaction are comparatively high reaction temperatures of 580-640° C. and a broad spectrum of sulfur-containing reaction products for example hydrogen sulfide.

According to U.S. Pat. No. 4,864,074 to Han et al., sulfur is reacted with methane to give methyl mercaptan and higher hydrocarbons over aluminum oxide and zeolites. In this process too, hydrogen sulfide forms in stoichiometric amounts.

The direct reaction of mixtures obtained in other processes, which comprise methane or higher, especially saturated, hydrocarbons, with or without water, hydrogen and sulfur compounds, especially carbon disulfide, to methyl mercaptan, has to date not been possible in industrially relevant yields and selectivities, but instead leads to a multitude of by-products. There is a need for purification processes, some of them complex, in which a multitude of secondary components cannot be recycled into the process. This reduces the overall selectivity for methyl mercaptan and hence the economic viability of the process.

The reaction of hydrocarbons with sulfur is always accompanied by the formation of hydrogen sulfide. This constitutes a significant disadvantage since the hydrogen sulfide obtained, according to the prior art, cannot be utilized in another process and has to be converted to elemental sulfur and water by means of combustion with air or oxygen in the manner of a Claus-like reaction. Owing to the additional capital cost of an $H_2S$ regeneration plant (Claus process) and the loss of the hydrogen component of value in the $H_2S$ combustion, this reduces the overall economic viability of the process.

It is an object of the present invention to provide an economically viable process for preparing methyl mercaptan from mixtures which comprise especially hydrocarbons and sulfur, wherein the hydrogen sulfide obtained is utilized in an economically viable manner. The carbon disulfide which forms as an intermediate can also originate from other sources.

The invention provides a process for preparing methyl mercaptan, comprising the steps of
a) hydrogenating carbon disulfide with water and
b) reacting the hydrogen sulfide formed in this reaction with at least one of the compounds selected from the group consisting of aldehydes, ethers, alcohols, CO, $CO_2$, $CO+CO_2$ and COS, in the presence of a metal oxide catalyst. The reaction with the carbon oxides is effected in the presence of hydrogen. The further oxygen compounds mentioned should preferably be used as a co-feed in this case.

This process can preferably follow the preparation of the carbon disulfide. Carbon disulfide can explicitly also be obtained via the disproportionation of carbonyl sulfide (COS) to carbon disulfide ($CS_2$) and carbon dioxide.

The reaction mixture obtained in the preparation of carbon disulfide comprises, in addition to the in the any unconverted sulfur and hydrocarbon(s), carbon disulfide, the hydrogen sulfide formed simultaneously and possibly further compounds, and is referred to as the reactant mixture.

In a preferred embodiment, the methyl mercaptan formed in the hydrogenation of the carbon disulfide is removed before the conversion of the hydrogen sulfide present in the reaction mixture formed to methyl mercaptan.

The hydrogenation of the carbon disulfide takes place at a reaction pressure of at least 5 bar gauge, especially up to 50 bar gauge, and a temperature of at least 200° C., especially up to 350° C., where the molar $CS_2/H_2/H_2S$ ratio is in the range from 1:1:1 to 1:10:10, preferably in the range from 1:2:2 to 1:5:5.

The hydrogen present in excess serves as a reaction component in the subsequent reaction of hydrogen sulfide with CO and/or $CO_2$ and need only be added there if required.

The economic viability of the overall process for preparing methyl mercaptan, which proceeds via carbon disulfide as a precursor, depends crucially on the product selectivity for methyl mercaptan, based on the carbon source used. The inventive use of carbon compounds which are obtained as secondary components of, or as waste streams in, other processes or have to date been utilized only as a fuel for energy generation can achieve an additional cost advantage. Examples of sources of these starting mixtures for preparing carbon disulfide are natural gases which comprise sulfur-containing components (e.g. $H_2S$, COS) as impurities, and carbon disulfide-containing streams. The mixtures generally comprise preferably methane and one or more saturated or unsaturated hydrocarbons with a $C_2$-$C_6$ radical. Further sources used for starting mixtures are industrial processes for obtaining organic nitrogen or sulfur compounds, in which relatively large amounts of by-products are obtained, but which must generally, according to the prior art, be incinerated without further addition of value or disposed of in some other way. More particularly, in the process according to the invention, offgas streams which are obtained in such processes and comprise, for example, $H_2S$, COS, $SO_2$, $SO_3$-containing compounds, alkyl sulfides or alkyl polysulfides can be used. These explicitly also include gases which are obtained from offgas streams from plants for generating energy or chemical products, directly or via separation techniques, or arise within biological metabolism processes (e.g. fermentation and degradation processes). These gas mixtures may comprise, as main components, hydrocarbons, especially methane, carbon oxides, organic sulfur and nitrogen compounds or hydrogen sulfide, as well as further compounds, and are used with preference in the process according to the invention.

The direct reaction of starting mixtures, for example, natural gas with methane as the main component, hydrocarbons, for example, from heavy oil fractions, residues from crude oil refining or higher hydrocarbons in general, for example oligomers, polymers or polycyclic aromatics, which are normally obtained, for example, also as waste streams in other chemical processes, with sulfur and the subsequent hydrogenation of the carbon disulfide to methyl mercaptan with further conversion of the hydrogen sulfide formed at the same time is the subject of the invention. Owing to significantly lower raw material costs, it has a significant cost advantage in the variable operating costs. The hydrocarbons used are, individually or in a mixture: alkanes having 1 to 20 carbon atoms, especially having 1 to 8, preferably having 1 to 4 carbon atoms, especially methane as the main constituent of the hydrocarbons, with 30 to 100% by volume, saturated cyclic or unsaturated cyclic hydrocarbon compounds, which also include polycyclic aromatics.

The ether used is preferably diethyl ether, the aldehyde formaldehyde.

The alcohols include methanol, ethanol, propanol, alcohols having 1-10 carbon atoms and at least one hydroxyl group, polyols and especially methanol.

In one embodiment, the invention is notable in that hydrogen sulfide, which forms, for example, during methyl mercaptan formation from carbon disulfide, is converted by preferably simultaneous reaction with carbon- and oxygen-containing compounds to methyl mercaptan, and need not be worked up by a downstream Claus process to give sulfur or in some other way.

The carbon compounds or hydrocarbons can be provided in the solid, liquid or gaseous state, but are preferably in gaseous form at the time of the reaction. Advantageously, the hydrocarbon-supplying source fed as the reactant to the process for preparing carbon disulfide is natural gas with methane or ethane as the main constituent. In addition, the reactant gas may comprise organic sulfur compounds or $H_2S$. Likewise present are generally inert gases, for example nitrogen.

The reaction of these gas mixtures with sulfur is effected without further workup of the gases at a reaction pressure of at least 5 bar, especially 5 to 50 bar, and a temperature of at least 200° C., especially 300-600° C., with liquid or gaseous sulfur in a one-stage or multistage process step, optionally in the presence of a catalyst known from the prior art, for example Co—Ni systems or H-ZSM5-zeolites.

Sulfur is used with an excess of 1 to 30% compared to the stoichiometrically necessary amount.

Carbon disulfide results as the main product of this reaction. By-products which may be obtained are sulfides, polysulfides and thiols. Since the reactant mixture comprises hydrogen-containing components, the $H_2S$ coproduct is always formed.

In the same process step, or optionally a further process step, the reaction mixture thus obtained is reacted with hydrogen at a reaction pressure of at least 5 bar, especially 5 to 50 bar, and a temperature of at least 200° C., especially 250° C. to 450° C., over a catalyst to give a reaction mixture which comprises methyl mercaptan as the main product and further hydrogen sulfide.

Before the conversion thereof, the methyl mercaptan is preferably removed from the reaction mixture by processes known per se.

Carbon disulfide can explicitly also be obtained via the disproportionation of carbonyl sulfide (COS) to carbon disulfide ($CS_2$) and carbon dioxide. Carbonyl sulfide is obtained, inter alia, in the reaction of carbon oxides (CO, $CO_2$) with sulfur. The hydrogenation of carbon disulfide thus formed, which may also be present in mixtures with carbonyl sulfide, is effected in a manner analogous to that described above.

As explained above, the problem to be solved in the reaction of hydrocarbons with sulfur and the reaction of carbon disulfide with hydrogen is the inevitable occurrence of the $H_2S$ coproduct. In the process according to the invention, the feeding of oxygen compounds, preferably alcohols, ethers or aldehydes, especially methanol, dimethyl ether or formaldehyde, carbonyl sulfide or carbon oxides (CO, $CO_2$, CO+$CO_2$), causes this $H_2S$ to be utilized in material form to form methyl mercaptan, such that the overall yield of methyl mercaptan, based on the carbon used, increases. As a result, the process can be operated in a particularly economically viable manner, since a costly workup of the hydrogen sulfide with a subsequent conversion to elemental sulfur (for example in a Claus reactor) is dispensed with. In addition, this can significantly reduce the holdup of $H_2S$ in the plant, which constitutes a significant safety advantage.

Following the conversion of the hydrogen sulfide, after removal of the methyl mercaptan, the unconverted feedstocks or intermediates, for example, carbon disulfide, are recycled into the process.

The overall selectivity for the formation of methyl mercaptan is increased by recycling the carbon, hydrogen and sulfur compounds into the process.

It is a particular advantage of the invention that (poly) sulfides are obtained with selectivities less than 1% and, as a result of the recycling into the process, carbon disulfide, for example, which is toxic, need not be separated in a complicated manner.

The product gas mixture of the last process step for conversion of the hydrogen sulfide comprises, as well as the methyl mercaptan and water formed, unconverted starting materials, for example, methane and possibly other hydrocarbons, methanol, hydrogen, and traces of carbon dioxide, carbon monoxide and by-products such as carbonyl sulfide, dimethyl sulfide and also small amounts of polysulfides (dimethyl disulfide) and carbon disulfide. Gases which are inert for the purposes of the reaction, for example, nitrogen, are also present in the product gas.

The methyl mercaptan formed is removed from the product gas mixture, for example as explained in DE-A-1768826, preferably in a plurality of distillation and scrubbing columns at temperatures between 10 and 140° C. Carbon dioxide, carbon monoxide, hydrogen, hydrogen sulfide and, as by-products, carbonyl sulfide, dimethyl sulfide and also small amounts of polysulfides (dimethyl disulfide) and carbon disulfide, are recycled into the process. Advantageously, this stream is reacted in an optional process step, preferably catalytically, with water in such a manner that the cycle gas recycled into the process comprises only one or more of the main methanol, $CS_2$, $CO_2$, CO, $H_2$ and $H_2S$ components, which can be converted to methyl mercaptan under the process conditions described.

The economic viability of the overall process is increased by virtue of the fact that advantageously, no inconvenient and costly removal of potential catalyst poisons, for example, sulfur compounds and elemental sulfur, is needed before the metered addition of the reactant mixture to the process. Likewise absent is a removal of such compounds after the reaction in the process stage to form carbon disulfide. These substances can be fed directly to the process together with the reaction gases recycled, without further workup and compression of the gases, which constitutes a significant cost advantage with regard to the capital and operating costs of the process. Advantageously, sulfur or sulfur-containing slags, which may be obtained as by-products of the process, can be fed directly in solid, liquid or gaseous form as a reactant to the process. These explicitly also include gases which are obtained from offgas streams from plants for generating energy or chemical products, directly or via separation techniques, or arise in the context of biological degradation and metabolism processes, and can be fed directly to the second process step. These gas mixtures may comprise, as main components, hydrocarbons, alcohols, carbon oxides, sulfur and nitrogen compounds in a total concentration of 5 to 90% by volume, especially 50 to 90% by volume, as well as other substances.

The reaction of the gas mixture with liquid or gaseous sulfur can optionally be effected using a catalyst, by reaction in a one-stage or multistage process step.

For the conversion of carbon disulfide to methyl mercaptan, a full conversion of hydrogen is preferably not pursued. The reaction is performed such that, after the reaction, the molar $CS_2/H_2/H_2S$ ratio is 1:1:1 to 1:10:10, especially 1:1:1 to 1:5:10. Advantageously, the reaction gas from the reaction of the hydrocarbons with sulfur leaves this process step at a pressure of at least 5 bar, especially 5 to 50 bar and can be fed directly without further compression to the hydrogenation. This constitutes a significant cost advantage since it is possible to dispense with a compressor stage with high capital and operating costs. Optionally, apparatus for removing elemental sulfur or sulfur-containing by-products may be connected upstream of the hydrogenation.

The subsequent conversion of hydrogen sulfide to methyl mercaptan is effected in a further process step over catalysts. However, it has been found to be an advantageous variant to remove the hydrogen sulfide beforehand from the reaction mixture which forms in the present reactions. Metal oxide catalysts have been found to be advantageous for the reaction for this purpose. Preference is given to using catalysts based on alkali metal molybdates or alkali metal tungstates, which may be applied to supports (U.S. Pat. No. 5,852,219). Especially suitable are supported catalysts which comprise oxidic molybdenum and potassium compounds, where Mo and K may be present in one compound, for example $K_2MoO_4$, and comprise at least one active oxidic compound of the general formula $A_xO_y$. A here is an element from the manganese, chromium or iron group, especially Mn or Re, and x and y are each integers from 1 to 7. The catalyst comprises the compounds preferably in a weight ratio of
$A_xO_y/K_2MoO_4$/support=(0.001-0.5)/(0.01-0.8)/1 or
$A_xO_y/MoO_3/K_2O$/support (0.0001-0.5)/(0.01-0.8)/(0.005-0.5)/1 the weight ratios preferably being in the range of
$A_xO_y/K_2MoO_4$/support=(0.001-0.3)/(0.05-0.5)/1 or
$A_xO_y/MoO_3/K_2O$/support=(0.001-0.3)/(0.05-0.3)/0.03-0.3/1.

These catalysts preferably comprise one or more promoters selected from the group of oxidic compounds of the general formula $M_xO_y$, in which M is a transition element or a metal from the group of the rare earths, and x and y are each integers from 1 to 7, according to the degree of oxidation of the elements M used.

M is preferably Fe, Co, Ni, La or Ce. In a particular embodiment, M may also be Rb, Cs, Mg, Sr and Ba. The ratios of the proportions by weight are in the ranges of:
$K_2MoO_4/M_xO_y$/support=(0.01-0.80)/(0.01-0.1)/1,
$MoO_3/K_2O/M_xO_y$/support=(0.10-0.50)/(0.10-0.30)/(0.01-0.1)/1.

When these catalysts are exposed to an $H_2S$-containing atmosphere before use, the oxidic metal compounds, which do not mean the support material, are converted to sulfidic compounds or mixtures of oxidic and sulfidic compounds, which are likewise usable in accordance with the invention.

The support materials used are preferably silicon dioxides, aluminum oxides, titanium dioxide, zeolites or activated carbons.

Titanium dioxide is preferably used with an anatase content of 60 mol %.

The preparation is effected in a multistage impregnation process, with which soluble compounds of the desired promoters or active oxidic compounds are applied to the support. The impregnated support is subsequently dried and optionally calcined.

The reaction of the hydrocarbons with sulfur and the hydrogenation of the carbon disulfide to methyl mercaptan are preferably combined in one reaction apparatus. This can be done using different or identical catalysts. Advantageously, bubble columns, trickle-bed reactors, reactive distillations, fixed bed reactors, staged reactors or tube bundle reactors are used for the catalyzed conversion to methyl mercaptan.

The conversion to methyl mercaptan is effected preferably over catalysts based on alkali metal molybdates or alkali metal tungstates. At a temperature of 200 to 600° C., preferably 250 to 400° C. and a pressure of 1.5 to 50 bar, preferably 8 to 40 bar. Catalysts which are used advantageously are described in applications WO 2005/040082, WO 2005/021491, WO 2006/015668 and WO 2006/063669.

In a further embodiment of the invention, the reaction with sulfur and the hydrogenation to methyl mercaptan are combined in one apparatus.

The product gas mixture can be separated by different known processes. A particularly advantageous separation is described in patents EP-B-0850923 (U.S. Pat. No. 5,866, 721).

Unconverted hydrocarbons, alcohols, carbon oxides, carbon disulfide, hydrogen and hydrogen sulfide, and also gaseous by-products, for example carbonyl sulfide, are recycled into the process. This is done in such a way that the compounds mentioned are fed in prior to the methyl mercaptan formation from carbon disulfide, and are reacted there in situ with hydrogen sulfide, which is obtained as a coproduct in the hydrogenation of carbon disulfide, to give methyl mercaptan. Otherwise, the recycling is effected by feeding into the reactant gas. Advantageously, prior to recycling into the process, the $CO_2(COS)/CO/H_2/H_2S$ ratio is adjusted by a reaction with water to 1:0.1:1:1 to 1:1:10:10. This can be done in a catalyzed or uncatalyzed manner in a fixed bed reactor, a reaction tube, a scrubbing column, or a reactive distillation at a temperature of at least 120° C.

Reaction components for example sulfides, polysulfides and hydrocarbons, which are obtained in the last process step during the removal of methyl mercaptan, can be recycled into the process without further workup, which increases the overall selectivity of the process for methyl mercaptan based on carbon, to more than 95%.

BRIEF DESCRIPTION OF THE DRAWINGS

FIG. 1 serves to further explain the process, wherein "Route a" denotes, in an illustrative manner, the reaction of methane with sulfur, hydrogen and methanol or $CO/CO_2$ to give methyl mercaptan and "Route b" the direct hydrogenation of carbon disulfide to methyl mercaptan with simultaneous reaction of hydrogen sulfide with methanol or $CO/CO_2$. What is important for the economic viability of the process is the possibility of using a multitude of solid, liquid and/or gaseous, carbon- and hydrogen-containing starting materials, which are reacted with sulfur in the process, and the fact that this stream need not be purified and desulfurized in a complicated manner. Moreover, all by-products which are removed after the reaction can be recycled into the process. Advantageously, if a sequential process regime is selected, all reactions proceed within the same pressure range, such that it is possible to dispense with a costly compression of the gases between the individual reaction steps. The reactions are effected at the starting pressure of the gases, under which they leave the first process step. Advantageously, this pressure is set to 5 to 50 bar, especially 8 to 40 bar. Gases which are inert for the purposes of the process are discharged continuously or discontinuously from the process via a purge gas stream.

EXAMPLES

Figure 1:
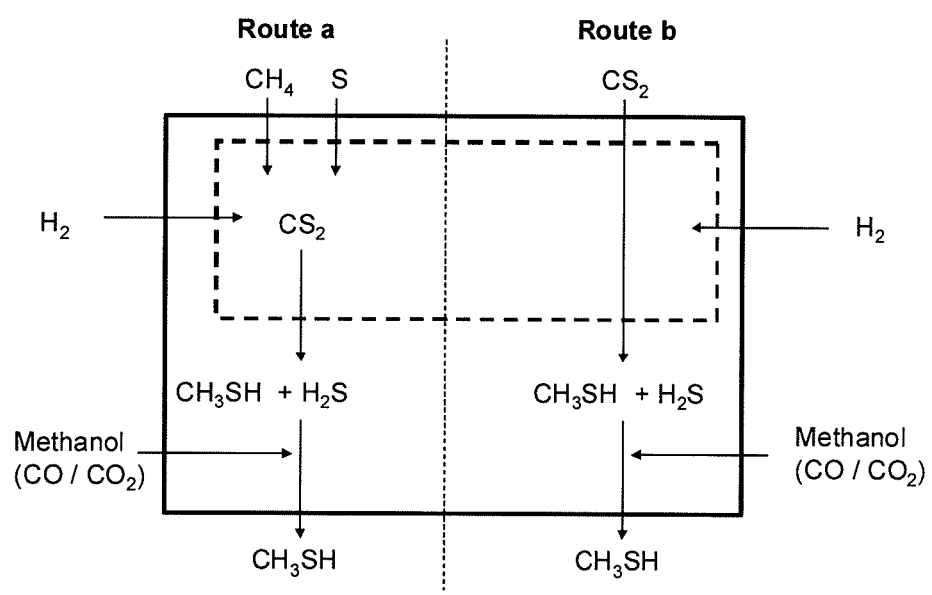
FIG. 1 schematically illustrates a process of an embodiment of the invention.

The process presented here comprises two stages.

In the first stage, methane was converted in liquid sulfur at a pressure of 15-50 bar and a temperature of 500-550° C. to carbon disulfide and hydrogen sulfide. This involved bubbling the methane through the liquid sulfur phase and cooling the product gas, immediately after it leaves the liquid phase, to approx. 150° C. by means of a cooler placed atop the reactor.

Hydrogen was added to the reaction product of the first stage, with the aid of which the carbon disulfide formed in the first stage was hydrogenated in the second stage at 15-50 bar and temperatures of 150-450° C. to methyl mercaptan. The reactants were provided in two ways:
1. $H_2S$ and $CS_2$ were prepared in a preliminary reactor from methane and sulfur. (Example 1)
2. $H_2S$ was prepared in a preliminary reactor from $H_2$ and sulfur, and $CS_2$ was added to the preliminary reactor by means of an HPLC pump. (Example 2)

The catalytic activity was determined for a single pass through the reactor.

Example 1

Sulfur was heated to 500° C. under a pressure of 15 bar, and a mixture of methane and nitrogen (1:1) was introduced. This procedure led to a methane conversion of 48.4% under steady-state conditions and hence to a product gas mixture consisting of 16.3% $CS_2$, 17.4% $CH_4$, 33.7% $N_2$ and 32.6% $H_2S$. Carbon-containing by-products were not observed (selectivity for $CS_2$=100%). Percentages in the case of gas mixtures should be interpreted as % by volume.

$H_2$ was added to this product mixture which was fed to the second stage. Thus, for the second stage, the reactant composition was 9% $CS_2$, 9.6% $CH_4$, 18.7% $N_2$, 18.2% $H_2S$ and 44.5% $H_2$. For the $K_2MoO_4/SiO_2$ catalyst, the conversions, yields and selectivities of this hydrogenation are reported as a function of temperature in Table 1 (reaction pressure p=15 bar).

TABLE 1

| Temp [° C.] | $CS_2$ conversion | Selectivity [%] | | | Yield [%] | | |
| --- | --- | --- | --- | --- | --- | --- | --- |
| | | $CH_4$ | MC | DMS | $CH_4$ | MC | DMS |
| 250 | 17.16 | 0.00 | 93.37 | 0.26 | 0.00 | 16.02 | 0.04 |
| 300 | 66.97 | 0.00 | 90.18 | 0.29 | 0.00 | 60.39 | 0.19 |
| 325 | 95.65 | 0.00 | 83.15 | 0.33 | 0.00 | 79.53 | 0.31 |
| 350 | 99.97 | 0.00 | 83.07 | 0.40 | 0.00 | 83.04 | 0.40 |
| 375 | 99.97 | 3.23 | 79.12 | 0.39 | 3.23 | 79.09 | 0.39 |
| 400 | 99.97 | 10.09 | 71.57 | 0.45 | 10.09 | 71.55 | 0.45 |

The product selectivities and yields which result for the overall process, based on the $CH_4$ used, are shown in Table 2.

TABLE 2

| Temp [° C.] | $CH_4$ conversion | Selectivity [%] | | | Yield [%] | | |
|---|---|---|---|---|---|---|---|
| | | $CS_2$ | MC | DMS | $CS_2$ | MC | DMS |
| 250 | 49.67 | 79.30 | 15.34 | 0.09 | 39.39 | 7.62 | 0.04 |
| 300 | 49.67 | 31.62 | 57.81 | 0.37 | 15.71 | 28.72 | 0.18 |
| 325 | 49.67 | 4.16 | 76.14 | 0.60 | 2.07 | 37.82 | 0.30 |
| 350 | 49.67 | 0.03 | 79.50 | 0.76 | 0.01 | 39.49 | 0.38 |
| 375 | 48.13 | 0.03 | 78.13 | 0.76 | 0.01 | 37.61 | 0.37 |
| 400 | 44.87 | 0.03 | 75.82 | 0.95 | 0.01 | 34.02 | 0.42 |

Example 2

The procedure was according to the above-described Option 2 (separate feeding of carbon disulfide). The conditions in the preliminary stage were selected such that, before the hydrogenation stage, a gas mixture of 12.7% $N_2$, 9.9% $CS_2$, 12.6% $H_2S$ and 64.8% $H_2$ was established. At 20 bar and a total flow rate of 18.6 ml/min, the following conversions, yields and selectivities for the hydrogenation were achieved for the catalyst (28% $K_2MoO_4/SiO_2$) as a function of the main reactor temperature (Table 3).

TABLE 3

| T [° C.] | $CS_2$ conversion [%] | Selectivity [%] | | | Yield [%] | | |
|---|---|---|---|---|---|---|---|
| | | MC | DMS | $CH_4$ | MC | DMS | $CH_4$ |
| 150 | 1.14 | 100 | 0 | 0 | 1.14 | 0 | 0 |
| 165 | 0.03 | 100 | 0 | 0 | 0.03 | 0 | 0 |
| 180 | 0 | 100 | 0 | 0 | 0 | 0 | 0 |
| 195 | 0.8 | 100 | 0 | 0 | 0.8 | 0 | 0 |
| 210 | 6.84 | 100 | 0 | 0 | 6.84 | 0 | 0 |
| 225 | 10.39 | 100 | 0 | 0 | 10.39 | 0 | 0 |
| 240 | 26.32 | 100 | 0 | 0 | 26.32 | 0 | 0 |
| 255 | 53.91 | 98.02 | 1.5 | 0.48 | 52.84 | 0.81 | 0.26 |
| 270 | 90.07 | 97.8 | 1.13 | 1.07 | 88.08 | 1.02 | 0.96 |
| 285 | 99.94 | 97.92 | 0.92 | 1.15 | 97.87 | 0.92 | 1.15 |
| 300 | 100 | 97.54 | 0.87 | 1.6 | 97.54 | 0.87 | 1.6 |
| 315 | 100 | 96.7 | 0.87 | 2.42 | 96.7 | 0.87 | 2.42 |
| 330 | 100 | 94.96 | 0.83 | 4.22 | 94.96 | 0.83 | 4.22 |
| 345 | 100 | 92 | 0.85 | 7.15 | 92 | 0.85 | 7.15 |
| 360 | 100 | 87.34 | 1.09 | 11.58 | 87.34 | 1.09 | 11.58 |
| 375 | 100 | 79.81 | 1.24 | 18.95 | 79.81 | 1.24 | 18.95 |
| 390 | 100 | 69.24 | 1.44 | 29.32 | 69.24 | 1.44 | 29.32 |
| 400 | 100 | 61.27 | 1.53 | 37.19 | 61.27 | 1.53 | 37.19 |

Example 3

Figure 2A:
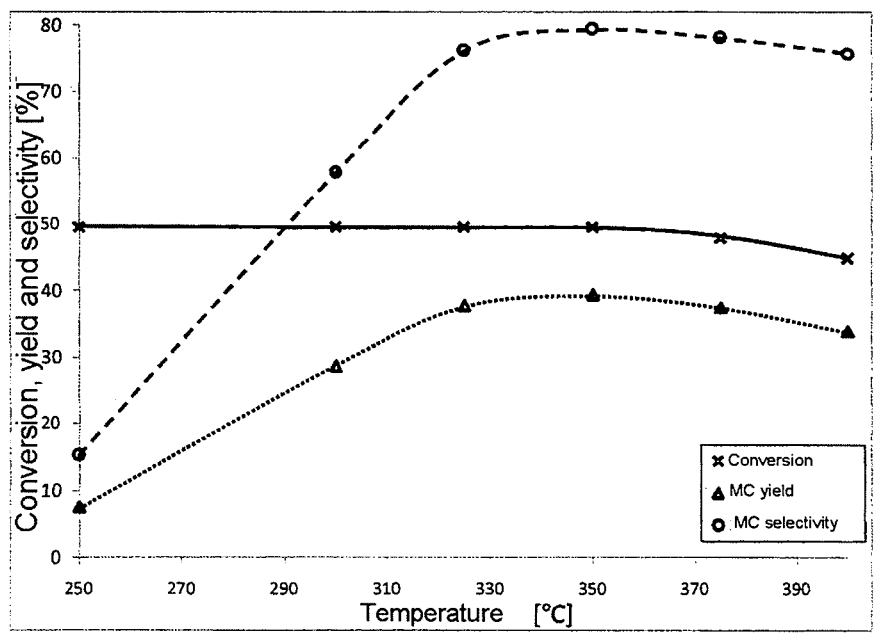
FIG. 2a shows the formation of carbon disulfide by the reaction of sulfur with methane at 525° C. with subsequent hydrogenation to methyl mercaptan over a catalyst which comprises 2.9 m % CoO and 28 m % $K_2MoO_4$ on an $SiO_2$ support.
Figure 2B:
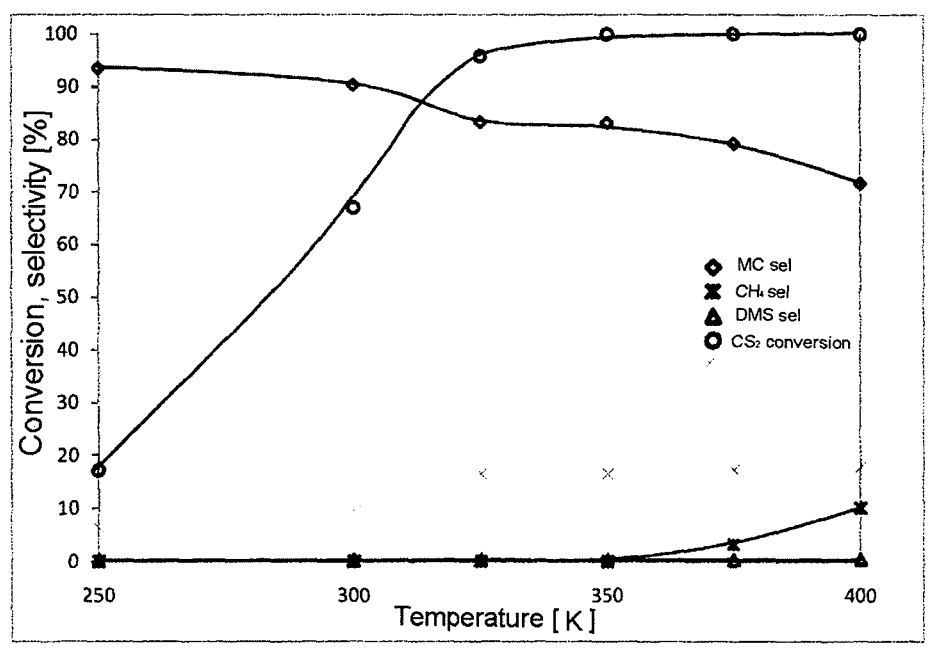
FIG. 2b shows the product selectivities and the $CS_2$ conversion for the hydrogenation step which follows the $CS_2$ formation.

FIG. 2a shows the formation of carbon disulfide by the reaction of sulfur with methane at 525° C. with subsequent hydrogenation to methyl mercaptan over a catalyst which comprises 2.9 m % CoO and 28 m % $K_2MoO_4$ on an $SiO_2$ support. FIG. 2b shows the product selectivities and the $CS_2$ conversion for the hydrogenation step which follows the $CS_2$ formation.

Example 4

When carbon disulfide is formed from methane and sulfur (Example 1), hydrogen sulfide is obtained as a coproduct ($CS_2:H_2S=1:2$). In the subsequent hydrogenation step to give methyl mercaptan (see Example 2), $H_2S$ is likewise formed as a coproduct. At a temperature of 325° C. and a reaction pressure of 15 bar (i) methanol, (ii) CO or (iii) $CO_2$, individually or together, at least in a total ratio of 1.1:1 ($MeOH+CO+CO_2$):$H_2S$ was supplied to the resulting product gas mixture in the presence of the hydrogen required. For all three reactants, an $H_2S$ conversion of >95% was observed with simultaneously increased methyl mercaptan yields. By increasing the methanol/CO or $CO_2$ content and recycling unconverted reactants (after removal of methyl mercaptan), it was possible to achieve full conversion of hydrogen sulfide.

The invention claimed is:

1. A process for preparing methyl mercaptan, comprising the steps of
   a) hydrogenating carbon disulfide and
   b) reacting the hydrogen sulfide, which is contained in the reaction mixture formed the reactions before, with at least one of the compounds selected from the group consisting of alcohols, ethers, and aldehydes, in the presence of a metal oxide catalyst, wherein hydrogen is only added if required,
   wherein said process is preceded by the reaction of carbon compounds or hydrocarbons with sulfur to give carbon disulfide and the formation of carbon disulfide is effected in the presence of a catalyst based on a Co—Ni system or an H-ZSM-5-zeolite.

2. The process as claimed in claim 1, wherein the methyl mercaptan is removed from the reaction mixture that is formed in the hydrogenation of the carbon disulfide.

3. The process as claimed in claim 1, wherein the carbon disulfide is converted at a reaction pressure of at least 5 bar and a temperature of at least 200° C.

4. The process as claimed in claim 1, wherein the hydrogen sulfide is reacted with methanol.

5. The process as claimed in claim 1, wherein the molar $CS_2/H_2/H_2S$ ratio after the hydrogenation of the carbon disulfide ranges from 1:1:1 to 1:10:10.

6. The process of claim 5, wherein said molar $CS_2/H_2/H_2S$ ratio ranges from 1:1:1 to 1:5:10.

7. The process as claimed in claim 1, wherein the hydrocarbons or carbon compounds originate from off-gas streams from processes for generating energy or chemical products.

8. The process as claimed in claim 1, wherein the hydrocarbons or carbon compounds originate from the workup of processes for oxidizing hydrocarbons and for synthesizing nitrogen and sulfur compounds.

9. The process as claimed in claim 1, wherein the hydrocarbons or carbon compounds originate from biological metabolism processes.

10. The process as claimed in claim 1, wherein the carbon disulfide is formed in the presence of liquid or gaseous sulfur, in a one-stage or multistage non-catalyzed homogeneous reaction or using a catalyst.

11. The process as claimed in claim 1, wherein, after removal of the methyl mercaptan, unconverted gaseous feed-stocks and by-products are removed and recycled into the process.

12. The process as claimed in claim 1, wherein the total amount of the hydrogen sulfide is adjusted by varying the carbon-hydrogen ratio of the compounds present in the reaction mixture or of the $H_2$ content in the reaction gas fed to the process, and by varying one or more of the process parameters selected from the group of: residence time, reaction temperature and reaction pressure.

13. The process as claimed in claim 1, wherein reactive distillations, bubble column reactors, fixed bed reactors, trickle bed reactors, staged reactors or tube bundle reactors are used for the catalyzed conversion to methyl mercaptan.

14. The process as claimed in claim 1, wherein the reaction of the hydrocarbons with sulfur and the hydrogenation of the carbon disulfide formed to methyl mercaptan are performed in one reaction apparatus.

15. The process as claimed in claim 1, wherein the reaction mixture which arises in the formation of carbon disulfide is supplied directly with no drop in a second process step tier hydrogenation of the carbon disulfide.

16. The process as claimed in claim 1, wherein the metal oxide catalyst is an alkali metal tungstate, alkali metal molybdate, or alkali metal molybdate comprising transition metal oxides or sulfides as promoters.

17. The process as claimed in claim 16, wherein at least one of the promoters selected from the group of oxides or sulfides of chromium, iron, cobalt, manganese and rhenium is present in the alkali metal tungstates, alkali metal molybdates or halogenated alkali metal tungstates or alkali metal molybdates.

18. The process as claimed in claim 1, wherein the metal oxide catalyst comprises molybdates or tungstates comprising transition metal and alkali metal oxides or sulfides as promoters.

19. The process as claimed in claim 1, wherein the metal oxide catalyst is a supported catalyst, which comprises oxidic molybdenum and potassium compounds, where Mo and K may be present in one compound, and which comprise at least one active oxidic compound of the general formula $A_xO_y$, A is one or more element from the iron or manganese group and x and y are each integers from 1 to 7.

20. The process of claim 19, wherein A is one or more elements selected from the group consisting of Co, Mn, and Re.

21. The process as claimed in claim 1, wherein molybdate- or tungstate-containing catalysts are used, which comprise transition metal and alkali metal oxides or sulfide as promoters.

22. The process as claimed in claim 1, wherein the hydrogenation of carbon disulfide is effected in the presence of a catalyst.

23. The process as claimed in claim 22, wherein the catalyst is an alkali metal molybdate or alkali metal tungstate.

24. The process of claim 1, wherein the at least one of the compounds reacted with the hydrogen sulfide is selected from the group consisting of methanol, dimethyl ether, and formaldehyde.

25. The process of claim 1, which results in the formation of methyl mercaptan with a selectivity of up to 98 percent.

* * * * *